(12) United States Patent
Olivieri et al.

(10) Patent No.: US 9,504,547 B2
(45) Date of Patent: Nov. 29, 2016

(54) IMPLANTABLE MEDICAL DEVICE AND METHODS OF DELIVERING THE IMPLANTABLE MEDICAL DEVICE

(75) Inventors: Steven A. Olivieri, Shrewsbury, MA (US); Peter J. Pereira, Mendon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 408 days.

(21) Appl. No.: 13/612,167

(22) Filed: Sep. 12, 2012

(65) Prior Publication Data
US 2013/0066146 A1    Mar. 14, 2013

Related U.S. Application Data

(60) Provisional application No. 61/533,588, filed on Sep. 12, 2011.

(51) Int. Cl.
*A61F 2/00* (2006.01)
*A61F 13/00* (2006.01)

(52) U.S. Cl.
CPC .................... *A61F 2/0045* (2013.01)

(58) Field of Classification Search
CPC .... A61F 2/0045; A61F 2/0036; A61F 2/005; A61F 2/0009; A61F 2/04; A61F 6/08; A61F 2250/0007; A61F 2250/0031; A61F 2002/047; A61F 2/004; A61B 2017/00805
USPC ........ 600/37, 29–32; 606/151; 128/897–899, 128/834, 885
See application file for complete search history.

(56) References Cited

U.S. PATENT DOCUMENTS

| | | |
|---|---|---|
| 4,669,473 A | 6/1987 | Richards et al. |
| 6,884,212 B2 | 4/2005 | Thierfelder et al. |
| 7,070,558 B2 | 7/2006 | Gellman et al. |
| 7,112,210 B2 | 9/2006 | Ulmsten et al. |
| 7,407,480 B2 | 8/2008 | Staskin et al. |
| 7,452,368 B2 | 11/2008 | Rudnick et al. |
| 7,645,227 B2 | 1/2010 | Smith et al. |
| 2003/0195386 A1* | 10/2003 | Thierfelder et al. ............ 600/37 |
| 2004/0225181 A1 | 11/2004 | Chu et al. |
| 2005/0096499 A1 | 5/2005 | Li et al. |
| 2005/0288689 A1 | 12/2005 | Kammerer |
| 2006/0229493 A1* | 10/2006 | Weiser et al. .................... 600/37 |
| 2007/0038018 A1* | 2/2007 | Chu ...................... A61F 2/0045 600/37 |
| 2007/0282160 A1 | 12/2007 | Sheu et al. |
| 2008/0196729 A1 | 8/2008 | Browning et al. |
| 2009/0171143 A1* | 7/2009 | Chu et al. ....................... 600/37 |
| 2010/0152530 A1 | 6/2010 | Timmer et al. |
| 2010/0261955 A1* | 10/2010 | O'Hern et al. .................. 600/37 |
| 2010/0261956 A1* | 10/2010 | Townsend et al. ............. 600/37 |
| 2012/0108894 A1* | 5/2012 | Young et al. ................... 600/37 |

OTHER PUBLICATIONS

Sand, "Histology of First Generation BioMesh", NorthShore University HealthSystem, 2009, 46 pages.

* cited by examiner

*Primary Examiner* — Navin Natnithithadha
*Assistant Examiner* — Sunita Reddy
(74) *Attorney, Agent, or Firm* — Brake Hughes Bellermann LLP

(57) ABSTRACT

A medical device and method of delivery of the medical device within a patient's body are disclosed by the present invention. The medical device includes a first elongate member and a second elongate member. A first portion and a second portion of the second elongate member are configured to form a defined non-planar shape such that the first portion is a first arm of the defined non-planar shape and the second portion is a second arm of the defined non-planar shape.

20 Claims, 14 Drawing Sheets

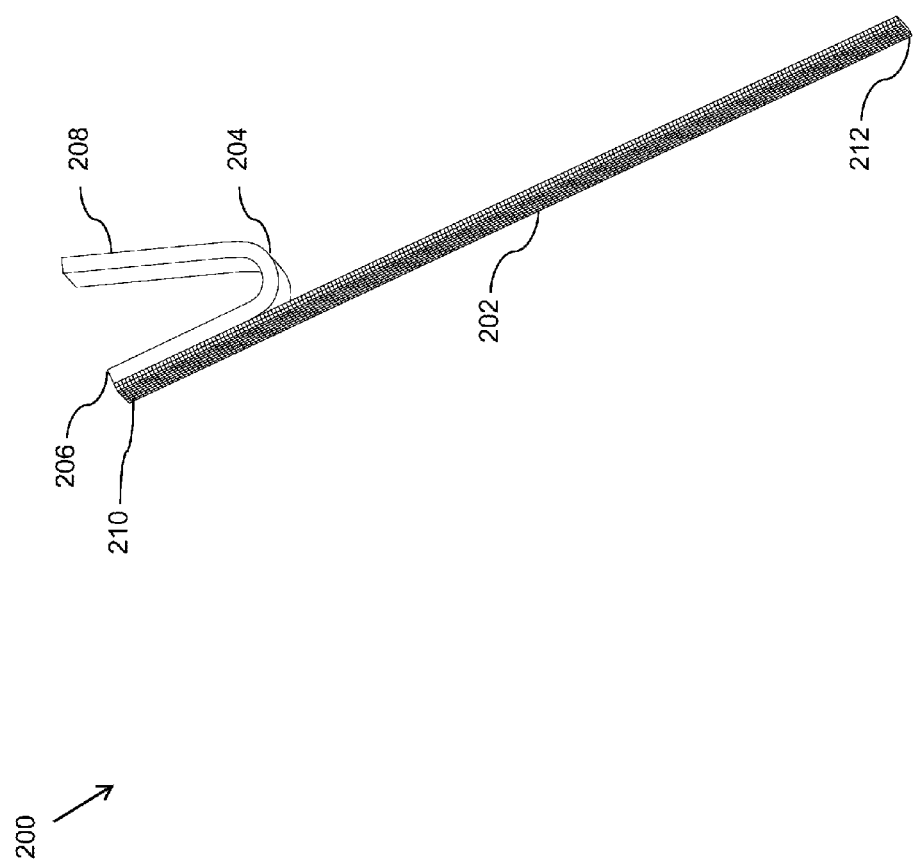

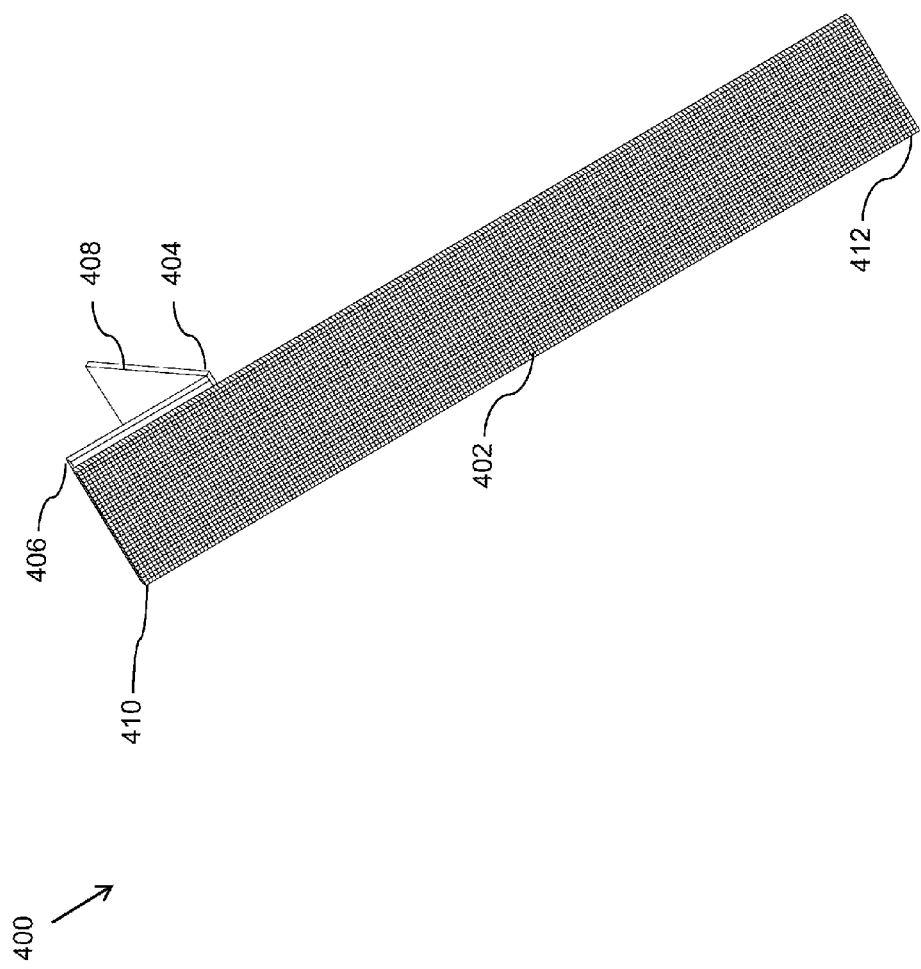

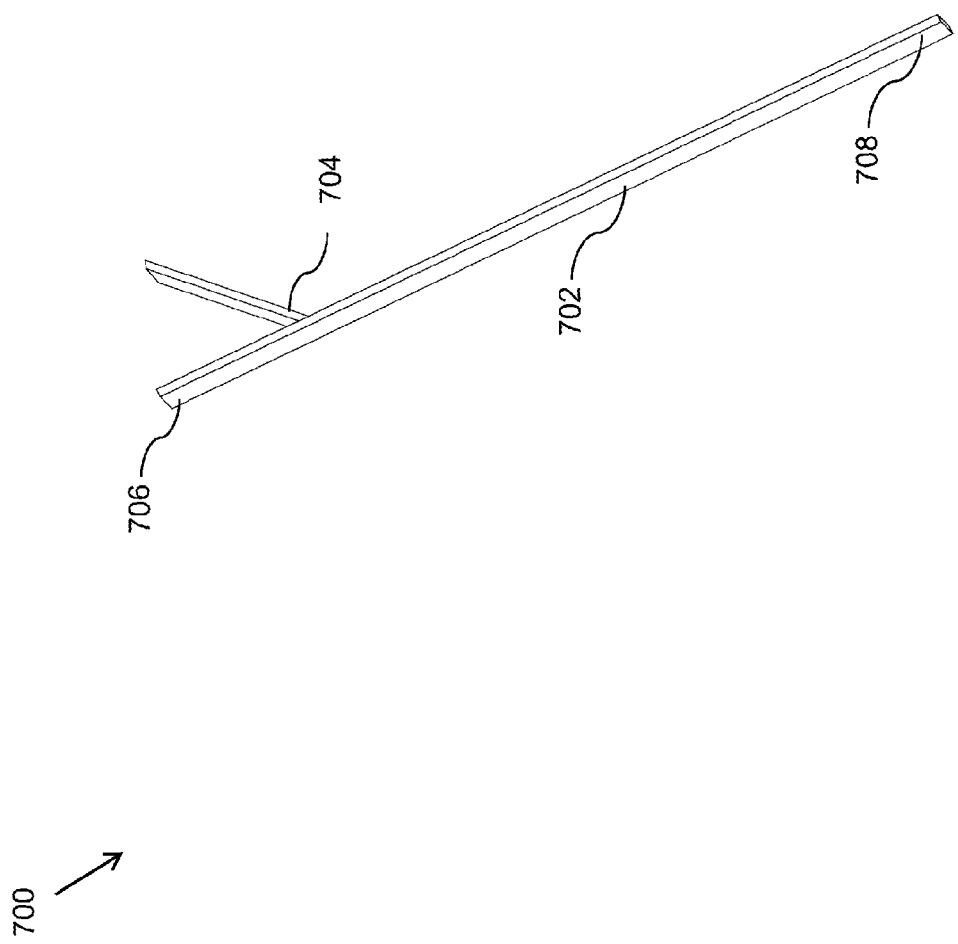

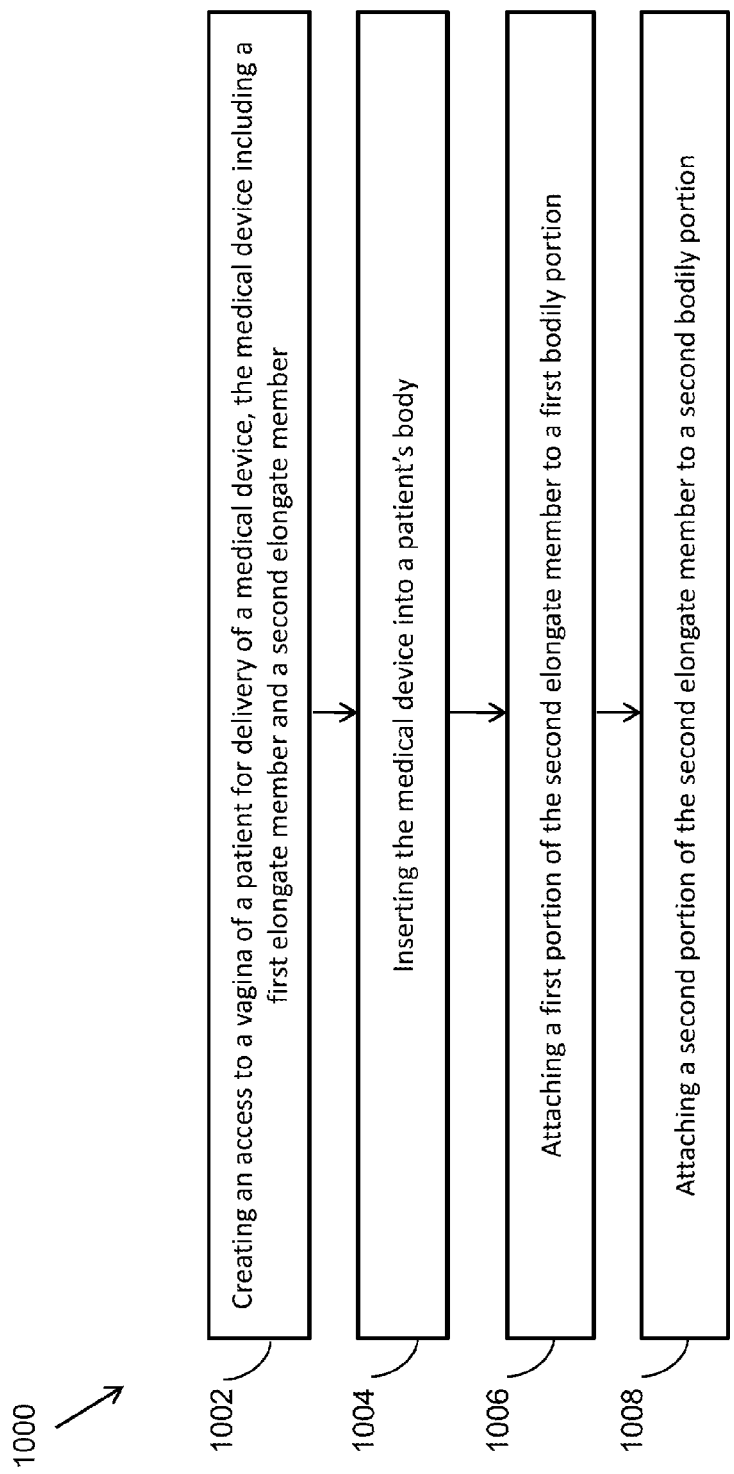

IMPLANTABLE MEDICAL DEVICE AND METHODS OF DELIVERING THE IMPLANTABLE MEDICAL DEVICE

CROSS-REFERENCE TO RELATED APPLICATION

This application is a Nonprovisional of, and claims priority to, U.S. Patent Application No. 61/533,588, filed Sep. 12, 2011, entitled "AN IMPLANTABLE MEDICAL DEVICE AND METHODS OF DELIVERING THE IMPLANTABLE MEDICAL DEVICE", which is incorporated by reference herein in its entirety.

BACKGROUND

Field

The present invention generally relates to medical devices and procedures, particularly devices configured to be delivered and placed into a patient's body for treatment of pelvic organ prolapse and the method for their delivery and placement.

Description of the Related Art

Genital prolapse or pelvic organ prolapse is the protrusion of the pelvic organs into or out of the vaginal canal. Pelvic floor prolapse affects many women in the US and almost all of them undergo at least one reconstructive pelvic surgery in their lifetime. Many of the cases may be the result of damage to the vaginal and pelvic support tissue by stretching or tearing of the connective tissue within the pelvic space due to childbirth, age, obesity, post-menopausal conditions or chronically elevated intra-abdominal pressure. The results are the distention of organs such as the bladder and rectum, into the vagina, as well as various stages of vaginal avulsion.

Surgical therapy/technique is usually performed for the treatment of pelvic organ prolapse. These techniques for prolapse treatment include plication of the torn connective tissues and re-suspension of the vagina/uterus. Some traditional suspension techniques include utero-sacral suspension and sacrospinus ligament suspension. Some procedures for vaginal suspension include sacrocolpopexy, where the vagina/uterus is suspended to the sacral promontory with an implanted graft material. The grafts have demonstrated improved long-term success of the repair.

Y-shaped mesh may be used as a graft to treat vaginal vault prolapse. The Y shaped mesh aids vaginal cuff suspension to the sacrum and provides long-term support. The procedure can be minimally invasive (Laparoscopic Sacral Colpopexy) or traditional (open sacral colpopexy). These Y shaped meshes may be made of various types of polymeric or biological materials. Various doctors/operators may prefer a particular type of implant to repair the pelvic damage depending on the surgical requirements and a patient's history. Some doctors/operators may choose a biologic graft over a synthetic polypropylene graft as the biologic graft minimizes erosion as opposed to synthetic meshes. Others may prefer synthetic grafts as they provide long-term reinforcement for support structures. The existing implants are available either as a biologic graft or polypropylene graft. These implants do not include both a polypropylene and a biological material for specific usage to specific anatomical locations.

Thus, there is a need for an improved polypropylene medical device/implant having biological material at specific locations to suit the anatomical structure.

SUMMARY

A medical device and method of delivery of the medical device within a patient's body are disclosed by the present invention. The medical device includes a first elongate member and a second elongate member. The first elongate member further includes a proximal end portion and a distal end portion. The first elongate member is made of a first material. The second elongate member includes a first portion and a second portion. The first portion of the second elongate member is attached to the first elongate member and the second portion of the second elongate member is attached to the first portion of the second elongate member at one of its transverse edge. The first portion and the second portion of the second elongate member are configured to form a defined non-planar shape such that the first portion is a first arm of the defined non-planar shape and the second portion is a second arm of the defined non-planar shape. The second elongate member is made of a second material different than the first material of the first elongate member.

BRIEF DESCRIPTION OF THE FIGURES

The invention and the following detailed description of certain embodiments thereof may be understood with reference to the following figures:

FIGS. 3A and 3B are further perspective views of the medical device of FIG. 2, in accordance with an embodiment of the present invention.

FIGS. 4A and 4B are perspective views of a medical device in accordance with an embodiment of the present invention.

FIG. 7 is a perspective view of a medical device in accordance with an embodiment of the present invention.

FIG. 10 is a flowchart illustrating a method of placement of a medical device, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including"

and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating vaginal prolapse. However, the invention may be equally employed for other treatment purposes such as pelvic organ prolapse. As described below in various illustrative embodiments, the invention provides systems, methods, and devices employing an improved medical device configured to be implanted within a patient's body to support pelvic organs for the treatment of pelvic prolapse.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, a human male, or any other mammal.

Figure 1:
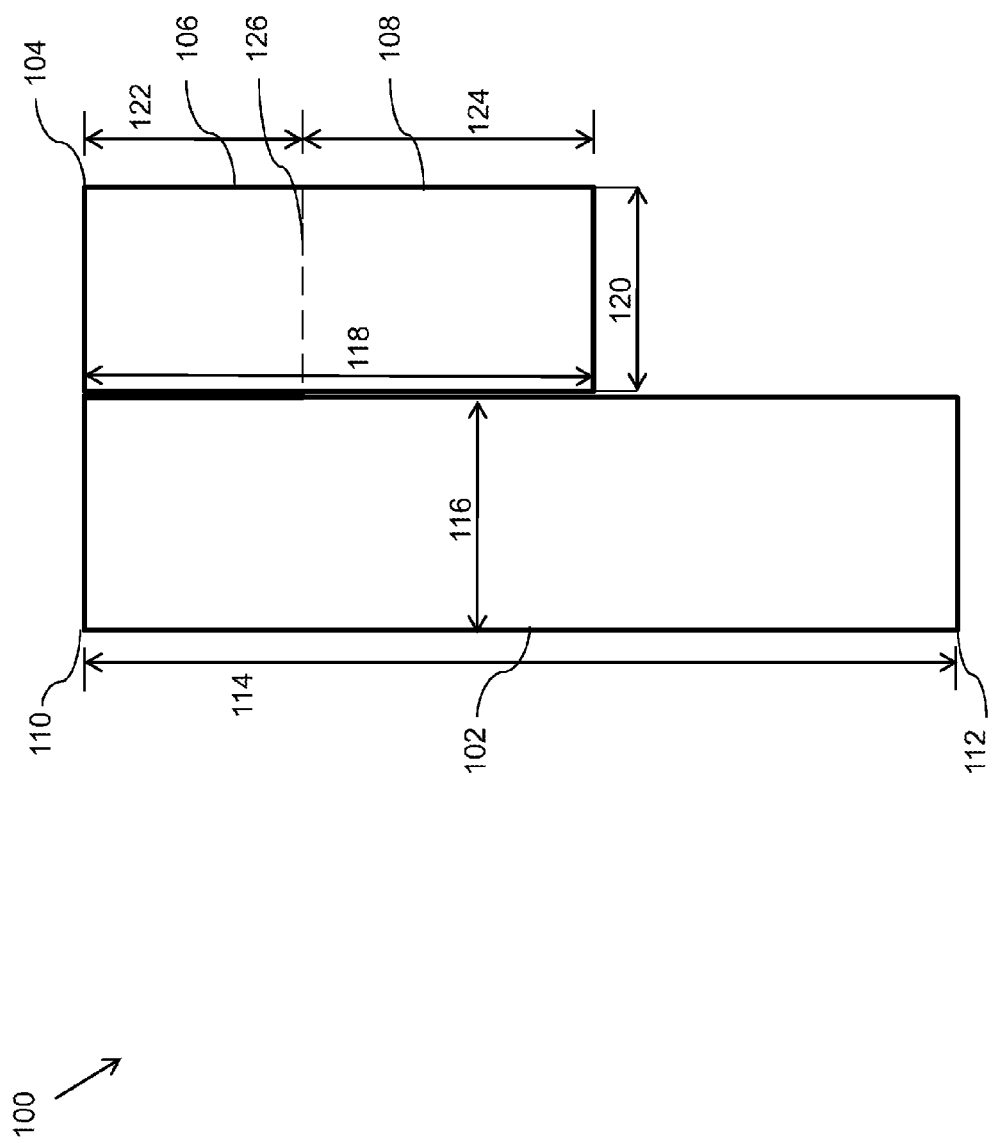
FIG. 1 is a schematic diagram of a medical device configured to be implanted within a patient's body, in accordance with an embodiment of the present invention.

FIG. 1 is a schematic diagram of a medical device 100 configured to be implanted within a patient's body. In some embodiments, the medical device is a bodily implant configured to support bodily tissues for the treatment of pelvic floor prolapse. The medical device 100 includes a first elongate member 102 and a second elongate member 104. The second elongate member 104 includes a first portion 106 and a second portion 108. The first portion 106 of the second elongate member 104 is attached to the first elongate member 102 and the second portion 108 of the second elongate member 104 is attached to the first portion 106 of the second elongate member 104 at one of its transverse edges such as the edge 126.

The first elongate member 102 includes a proximal end portion 110 and a distal end portion 112 with a length 114 extending between the proximal end portion 110 and the distal end portion 112. In some embodiments, the first elongate member 102 is a strip with the length 114 substantially more than its width 116. In certain embodiments, the first elongate member 102 is rectangular in shape. In other embodiments, the first elongate member 102 may have other shapes. In accordance with some embodiments, the width 116 of the first elongate member 102 is uniform from the proximal end portion 110 to the distal end portion 112. In other embodiments, the width 116 of the first elongate member 102 varies from the proximal end portion 110 to the distal end portion 112.

In accordance with some embodiments, the second elongate member 104 is a strip with its length 118 substantially more than its width 120. In certain embodiments, the second elongate member 104 is rectangular in shape. In other embodiments, the second elongate member 104 may have other shapes. In accordance with some embodiments, the width 120 of the second elongate member 104 is uniform from its proximal end portion to its distal end portion. In other embodiments, the width 120 of the second elongate member 104 varies from its proximal end portion to its distal end portion.

In some embodiments, the length 118 of the second elongate member 104 is lesser than the length 114 of the first elongate member 102. In some embodiments, the length 118 of the second elongate member 104 is half of the length 114 of the first elongate member 102. In other embodiments, the length 118 of the second elongate member 104 and the length 114 of the first elongate member 102 can be the same.

In some embodiments, the second elongate member 104 has width 120 equal to the width 116 of the first elongate member 102. In other embodiments, the second elongate member 104 has width 120 lesser to the width 116 of the first elongate member 102. Further, in some other embodiments, the second elongate member 104 has width 120 greater to the width 116 of the first elongate member 102.

As mentioned above, the second elongate member 104 further includes the first portion 106 and the second portion 108. In accordance with some embodiments, the width of the first portion 106 and the width of the second portion 108 are same and equal to the width 120 of the second elongate member 104. In other embodiments, the width of the first portion 106 can be different from the width of the second portion 108. In such cases, the second elongate member 104 is tapered from its distal end portion to the proximal end portion. Similarly, in some embodiments, the length 122 of the first portion 106 and length 124 of the second portion 108 can be the same. In other embodiments, the length 122 of the first portion 106 and the length 124 of the second portion 108 can be different.

The second elongate member 104 is configured to be attached to the first elongate member 102. In some embodiments, the first portion 106 of the second elongate member 104 is attached to the first elongate member 102. In some embodiments, the first portion 106 of the second elongate 104 member is attached to the first elongate member 102 by various attachment elements along the length. In other embodiments, the first portion 106 of the second elongate member 104 is attached to the first elongate member 102 at specific spots with the attachment elements. In some embodiments, the attachment elements include without limitations sutures, adhesives, bonding agents, mechanical fasteners (e.g. a medical grade plastic clip), and the like. These attachment elements may be provided at specific locations on the elongate members 102 and 104 to couple them at the desired locations. The sutures may be made of biological materials and/or synthetic materials. The sutures may be strong enough to hold both the first and second elongate members 102 and 104 securely, and may also be flexible enough to be knotted.

The second portion 108 of the second elongate member 104 is attached to the first portion 106 of the second elongate member 104 at one of its transverse edges 126. In some embodiments, the first portion 106 and the second portion 108 can form an integral part of the second elongate member 104 such that the first portion 106 and the second portion 108 form a part of a single strip. In other embodiments, the first portion 106 and the second portion 108 can be removably attached to form the second elongate member 104. Since the second portion 108 is attached with the first portion 106 at only one of its transverse edges 126, it is free to move or rotate with respect to the first portion 106 and can take a defined shape based on an anatomical location. The defined shape formed by moving/rotating the second portion 108 with respect to the first portion 106 is non-planar and can be modified based on the anatomical location of the patient where the first portion 106 and the second portion 108 are attached. Upon placement, the first portion 106 of the second elongate member 104, the second portion 108 of the second elongate member 104, and the distal end portion 112 of the first elongate member 102 act as different arms of the defined shape that are configured to support the pelvic organs at distinct bodily locations. In accordance with these embodiments, the first portion 106 forms a first arm of the defined shape, the second portion 108 forms a second arm of the defined shape and the distal end portion 112 of the first elongate member 102 forms a third arm of the defined shape.

The first portion 106 of the second elongate member 104 is configured to be attached to a first bodily portion and the second portion 108 of the second elongate member 104 is configured to be attached to a second bodily portion. In some embodiments, the first bodily portion is an exterior surface of an anterior vaginal wall and the second bodily portion is an exterior surface of a posterior vaginal wall of the patient. Therefore, in accordance with these embodiments, the first portion 106 of the second elongate member 104 is attached to the exterior surface of an anterior vaginal wall and the second portion 108 of the second elongate member 104 is attached to the exterior surface of a posterior vaginal wall.

In some embodiments, the distal end portion 112 of the first elongate member 102 is configured to be attached to a third bodily portion. In some embodiments, the third bodily portion is a sacrum of the patient. Therefore, in some embodiments, the distal end portion 112 of first elongate member 102 is configured to be attached to the sacrum.

In some embodiments, the first elongate member 102 is made of a first material. In some embodiments, the first material is a synthetic material. In some embodiments, the first elongate member 102 includes a polymeric mesh body. In other embodiments, the first elongate member 102 includes a polymeric planar body without mesh cells and structures. Exemplary polymeric materials are polypropylene, polyester, polyethylene, nylon, PVC, polystyrene, and the like. In some embodiments, the mesh body is made of a non-woven polymeric material. An example of the mesh utilized in the first elongate member 102 is Polyform® Synthetic Mesh developed by the Boston Scientific Corporation. The Polyform® Synthetic Mesh is made from uncoated monofilament macro-porous polypropylene. Typically, the mesh surface of the first elongate member 102 is smooth to avoid/reduce irritation on adjacent body tissues during medical interactions. Additionally, the mesh body is stretchable and flexible to adapt movements along the anatomy of the human body and reduce suture pullout. Furthermore, softness, lightness, conformity, and strength are certain other attributes required in the mesh body for efficient tissue repair and implantation. In some other embodiments, the first elongate member 102 can be made of natural materials such as biologic material or a cadaveric tissue and the like.

The second elongate member 104 is made of a second material. In some embodiments, the second material is a biologic material. Specifically, in some embodiments, the second elongate member 104 is made of transplants from the same species (Allografts) or other species (Xenografts). Exemplary biologic materials are bovine dermis, porcine dermis, porcine intestinal sub mucosa, bovine pericardium, a cellulose based product, cadaveric dermis, and the like. The example of Allograft materials utilized in the second elongate member 104 include Tutoplast®, Repliform®, DuraDerm®, Urogen®, and the like. The example of Xenograft materials utilized in the second elongate member 104 includes Xenoform®, Stratisis®, Dermatrix® and the like. The second elongate member 104 made of biologic materials provide minimal risk of erosion and repair.

In some other embodiments, the medical device 100 also includes a third elongate member. In some embodiments, the third elongate member is made of a biologic material. A few examples of the biologic materials are discussed above. The third elongate member is attached to the first elongate member 102 at its distal end portion 112 and is configured to be attached to the sacrum of the patient. In some embodiments, the third elongate member is attached to the first elongate member 102 separately by an operator. In other embodiments, the third elongate member can form a part of the medical device 100 such that the operator can use the medical device 100 as such without separately attaching the third elongate member.

In some embodiments, the elongate members 102 and/or 104 made of biologic materials are hydrated or moistened prior to the use of the medical device 100. This is because in some embodiments, the biologic material is kept as dry before use in order to maintain a sterile condition. Sufficient hydration of the biologic material is done to produce lubrication and tissue turgor during implantation and also to increase its malleability to take the shape of the anatomical structure where it is placed.

Figure 2:
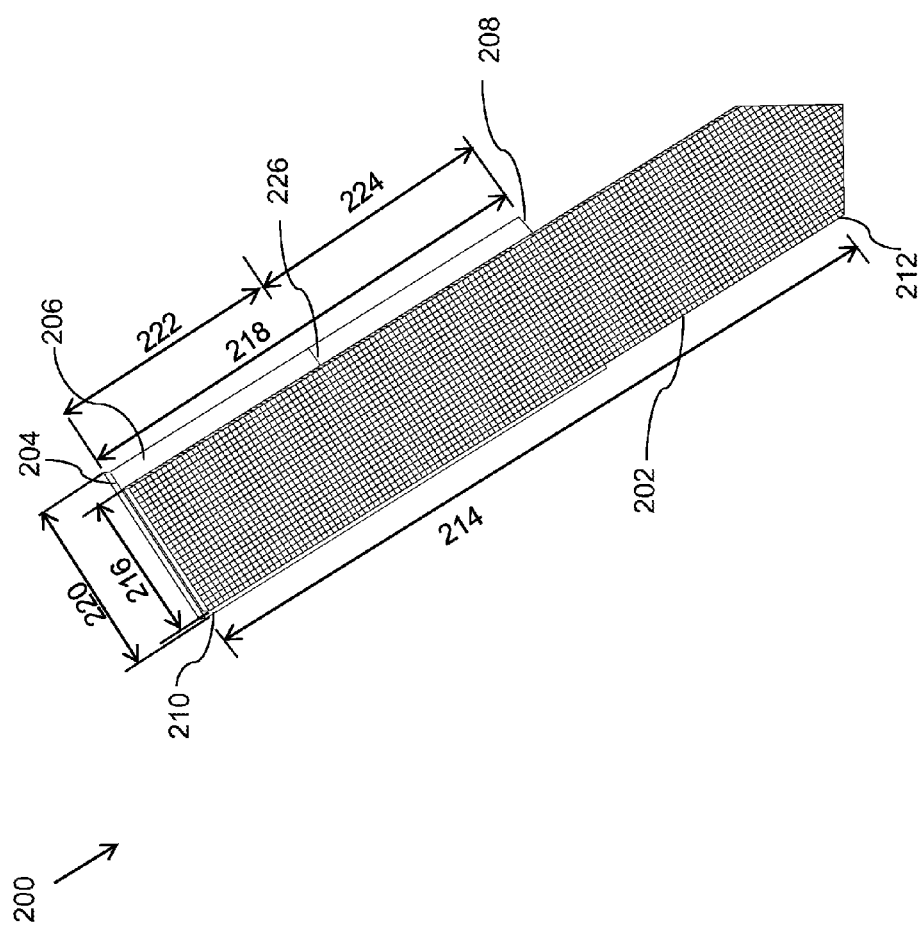
FIG. 2 is a perspective views of a medical device configured to be implanted within a patient's body, in accordance with an embodiment of the present invention.

FIG. 2 is a perspective view of a medical device 200 in accordance with an embodiment of the present invention. The medical device 200 includes a first elongate member 202 and a second elongate member 204. The second elongate member 204 includes a first portion 206 and a second portion 208. The first portion 206 of the second elongate member 204 is attached to the first elongate member 202 and the second portion 208 of the second elongate member 204 is attached to the first portion of 206 the second elongate member 204 at one of its transverse edges such as the edge 226.

The first elongate member 202 includes a proximal end portion 210 and a distal end portion 212 having a length 214 extending between the proximal end portion 210 and the distal end portion 212. In some embodiments, the first elongate member 202 is a strip with the length 214 substantially more than its width 216. In certain embodiments, the first elongate member 202 is rectangular in shape. In other embodiments, the first elongate member 202 may have other shapes. As shown, the width 216 of the first elongate member 202 is uniform from the proximal end portion 210 to the distal end portion 212. However, in other embodiments, the width 216 of the first elongated member 202 can vary from its proximal end portion 210 to its distal end portion 212.

In accordance with some embodiments, the second elongate member 204 is a strip with its length 218 substantially more than its width 220. As illustrated, the second elongate member 204 is rectangular in shape. However, in other embodiments, the second elongate member 204 may have other shapes. In accordance with some embodiments, the width 220 of the second elongate member 204 is uniform from its proximal end portion to its distal end portion. In other embodiments, the width 220 of the second elongate member 204 varies from the proximal end portion to the distal end portion.

In some embodiments, the second elongate member 204 has width 220 equal to the width 216 of the first elongate member 202. In other embodiments, the second elongate member 204 has width 220 lesser than the width 216 of the first elongate member 202. Further, in some other embodiments, the second elongate member 204 has width 220 greater than the width 216 of the first elongate member 202. Similarly, in some embodiments, the length 218 of the second elongate member 204 is lesser than the length 214 of the first elongate member 202. In some embodiments, the length 218 of the second elongate member 204 is half of the length 214 of the first elongate member 202. In other embodiments, the length 218 of the second elongate member 204 and the length 216 of the first elongate member 204 can be the same.

As mentioned above, the second elongate member 204 further includes the first portion 206 and the second portion 208. In accordance with some embodiments, the width of the first portion 206 of the second elongate member 204 and the width of the second portion 208 of the second elongate member 204 are the same and equal to the width 220 of the second elongate member 204. In other embodiments, the width of the first portion 206 can be different from the width of the second portion 208. In such cases, the second elongate member 204 may be tapered from its distal end portion to the proximal end portion. Similarly, in some embodiments, the length 222 of the first portion 206 and length 224 the second portion 208 can be same. In other embodiments, the length 222 of the first portion 206 and the length 224 of the second portion 208 can be different.

The shape of the first elongated member 202 and the second elongate member 204 described in conjunction with FIG. 1 and FIG. 2 is merely exemplary and various other shapes and designs are also possible in accordance with various embodiments of the present invention.

The second elongate member 204 is configured to be attached to the first elongate member 202. In some embodiments, the first portion 206 of the second elongate member 204 is attached to the first elongate member 202. In some embodiments, the first portion 206 of the second elongate member 204 is attached to the first elongate member 202 by various attachment elements along the length. In other embodiments, the first portion 206 of the second elongate member 204 is attached to the first elongate member 202 at specific spots. The first portion 206 of the second elongate member 204 can be attached to the first elongate member 202 through various attachment elements. In some embodiments, the attachment elements include without limitations sutures, adhesives, bonding agents, mechanical fasteners (e.g. a medical grade plastic clip), and the like. These attachment elements may be provided at specific locations on the elongate member 202 and 204 to couple them at the specific desired locations. The sutures may be made of biological materials and/or synthetic materials. The sutures may be strong enough to hold both the first elongate member 202 and the second elongate member 204 securely and may also be flexible enough to be knotted.

The second portion 208 of the second elongate member 204 is attached to the first portion 206 of the second elongate member 204 at one of its transverse edges 226. In some embodiments, the first portion 206 and the second portion 208 can form an integral part of the second elongate member 204 such that the first portion 206 and the second portion 208 form a part of a single strip. In other embodiments, the first portion 206 and the second portion 208 can be removably attached to form the second elongate member 204.

The first portion 206 of the second elongate member 204 is configured to be attached to a first bodily portion and the second portion 208 of the second elongate member 204 is configured to be attached to a second bodily portion. In some embodiments, the first bodily portion is an anterior vaginal wall and the second bodily portion is a posterior vaginal wall of the patient. Therefore, in accordance with these embodiments, the first portion 206 of the second elongate member 204 is attached to the exterior surface of the anterior vaginal wall and the second portion 208 of the second elongate member 204 is attached to the exterior surface of the posterior vaginal wall.

The distal end portion 212 of the first elongate member 202 is configured to be attached to a third bodily portion. In some embodiments, the third bodily portion is a sacrum of the patient. Therefore, the distal end portion 212 of first elongate member 202 is configured to be attached to the sacrum.

The first elongate member 202 is made of a first material. In some embodiments, the first material is a synthetic material. In some embodiments, the first elongate member 202 includes a polymeric mesh body. In other embodiments, the first elongate member 202 includes a polymeric planar body without mesh cells and structures. Exemplary polymeric materials are discussed in conjunction with FIG. 1. The second elongate member 204 is made of a second material. The second material is a biologic material. Exemplary biologic materials have been discussed in conjunction with FIG. 1. The second elongate member 204 made of biologic materials provide minimal risk of erosion and repair.

Figure 3B:
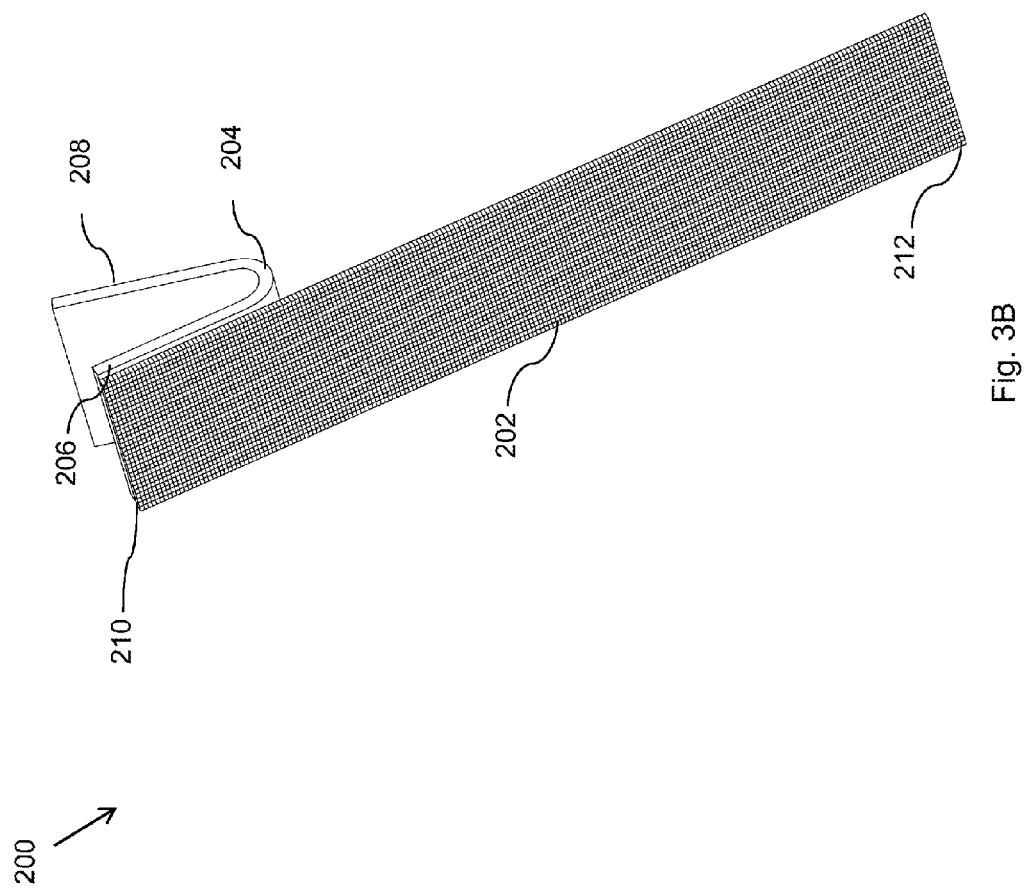

In accordance with various embodiments, since the second portion 208 is attached with the first portion 206 at only one of its transverse edges 226, it is free to move or rotate with respect to the first portion 206 and can take a defined shape based on an anatomical location. The defined shape formed by moving/rotating the second portion 208 with respect to the first portion 206 is non-planar and can be modified based on the anatomical location of the patient where the first portion 206 and the second portion 208 are attached. In some embodiments, the defined shape can be a U shape as illustrated in FIGS. 3A and 3B. FIGS. 3A and 3B illustrate perspective views of the medical device 200 with the second elongate member 204 forming a U shape. FIG. 3A illustrates the perspective view taken at an angle and FIG. 3B illustrates the perspective view taken at another angle.

In some embodiments, the second portion 208 of the second elongate member 204, which is attached to the first portion 206 of the second elongate member 204, is malleable. The malleable second portion 208 would allow the surgeon/operator to mould the second portion 208 over a portion of the vaginal vault as per the patient's anatomy.

Figure 4A:
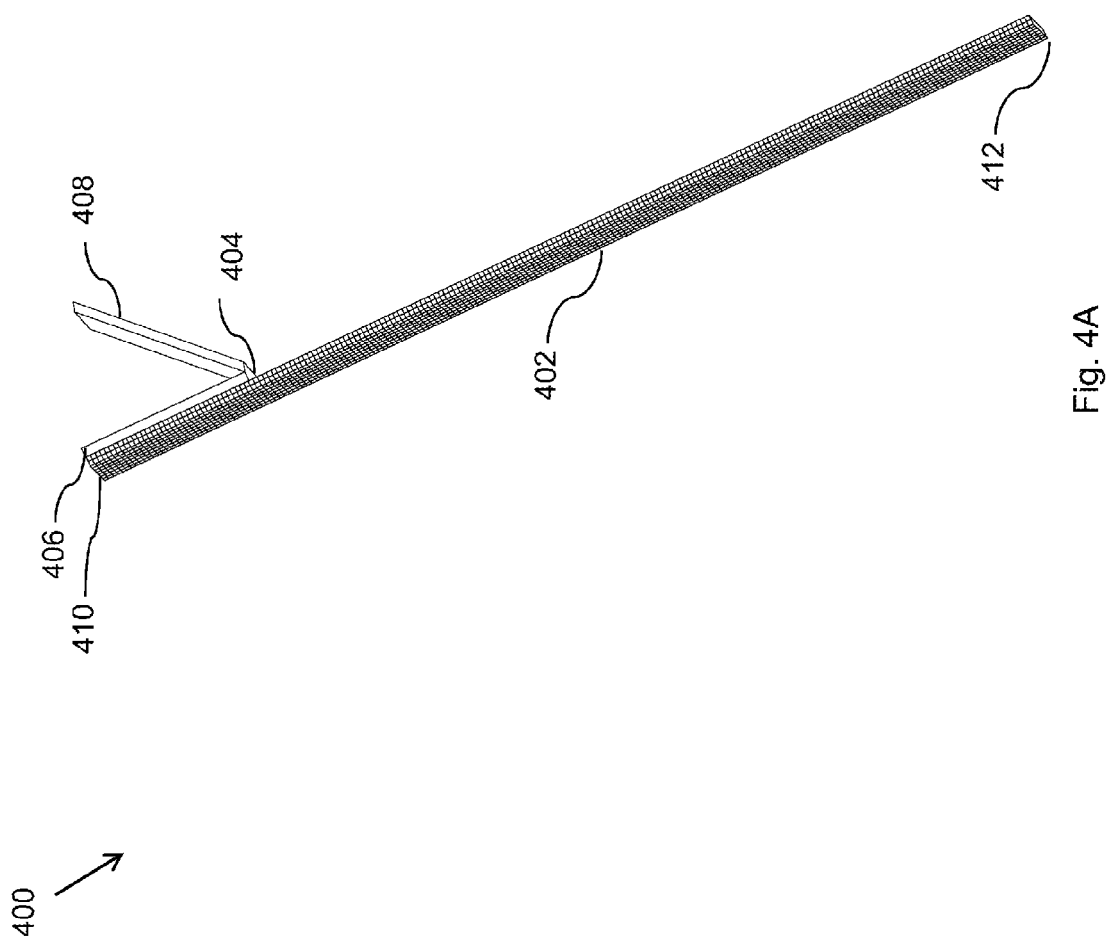

FIGS. 4A and 4B are perspective views of a medical device 400 in accordance with an embodiment of the present invention. The medical device 400 includes a first elongate member 402 and a second elongate member 404. The second elongate member 404 includes a first portion 406 and a second portion 408. The first portion 406 of the second elongate member 404 is attached to the first elongate member 402 and the second portion 408 of the second elongate member 404 is attached to the first portion 406 of the second elongate member 404 at one of its transverse edges. The first elongate member 402 and the second elongate member 404 are similar to those described in conjunction with FIGS. 1 and 2 above. In accordance with the illustrated embodiments, the first and second portions 406 and 408 of the second elongate member 404 are removably coupled. The first portion 406 and the second portion 408 can be attached to the first elongate member 402 and the first portion 406, respectively, through various attachment elements along the length. In some embodiments, the attachment elements include without limitations sutures, adhesives, bonding agents, mechanical fasteners (e.g. a medical grade plastic clip), and the like.

In accordance with various embodiments, since the second portion 408 is attached with the first portion 406 at only one of its transverse edges, it is free to move or rotate with respect to the first portion 406 and can take a defined shape based on an anatomical location. The defined shape formed by moving/rotating the second portion 408 with respect to the first portion 406 is non-planar and can be modified based on the anatomical location of the patient where the first portion 406 and the second portion 408 are attached. In some embodiments, the defined shape can be a V shape as illustrated in FIGS. 4A and 4B. These figures illustrate perspective views of the medical device 400 with the second elongate member 404 forming a V shape. FIG. 4A illustrates the perspective view taken at an angle and FIG. 4B illustrates the perspective view taken at another angle.

In some embodiments, the second portion 408 of the second elongate member 404, which is attached to the first portion 406 of the second elongate member 404, is malleable. The malleable second portion 408 would allow the surgeon/operator to shape the second portion 408 over a portion of the vaginal vault as per the requirement of the patient's anatomy.

As the portions 406 and 408 of the second elongate member 404 are made of biologic material, the surgeon/operator may need to hydrate them before the surgical procedure. This is because, in some embodiments, the biologic material is kept as dry before use in order to maintain a sterile condition. Sufficient hydration of the biologic material is required to produce lubrication and tissue turgor during implantation and also to facilitate shaping of the elongate members according to the shape of anatomical locations where they are attached.

Figure 5A:
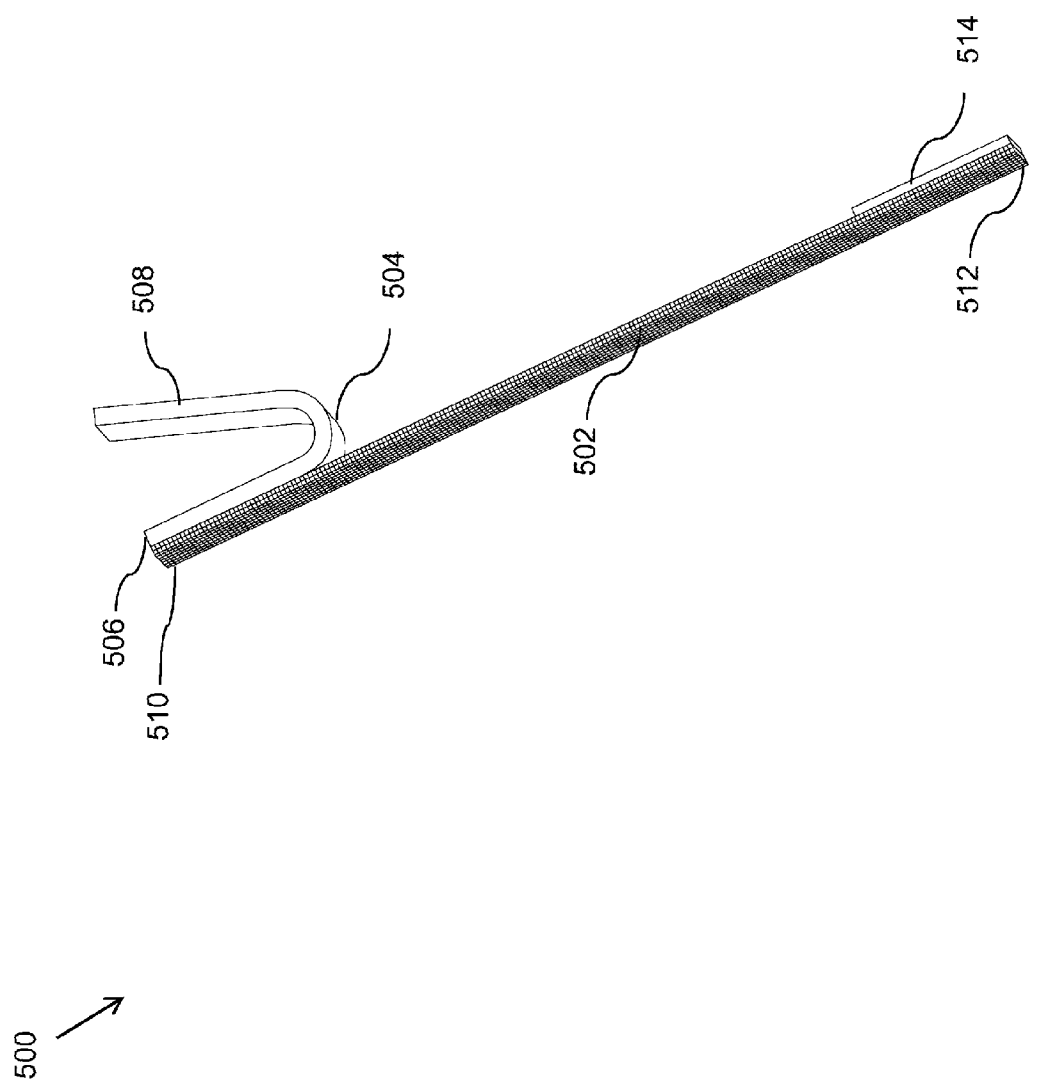
FIGS. 5A and 5B are perspective views of a medical device in accordance with an embodiment of the present invention.
Figure 5B:
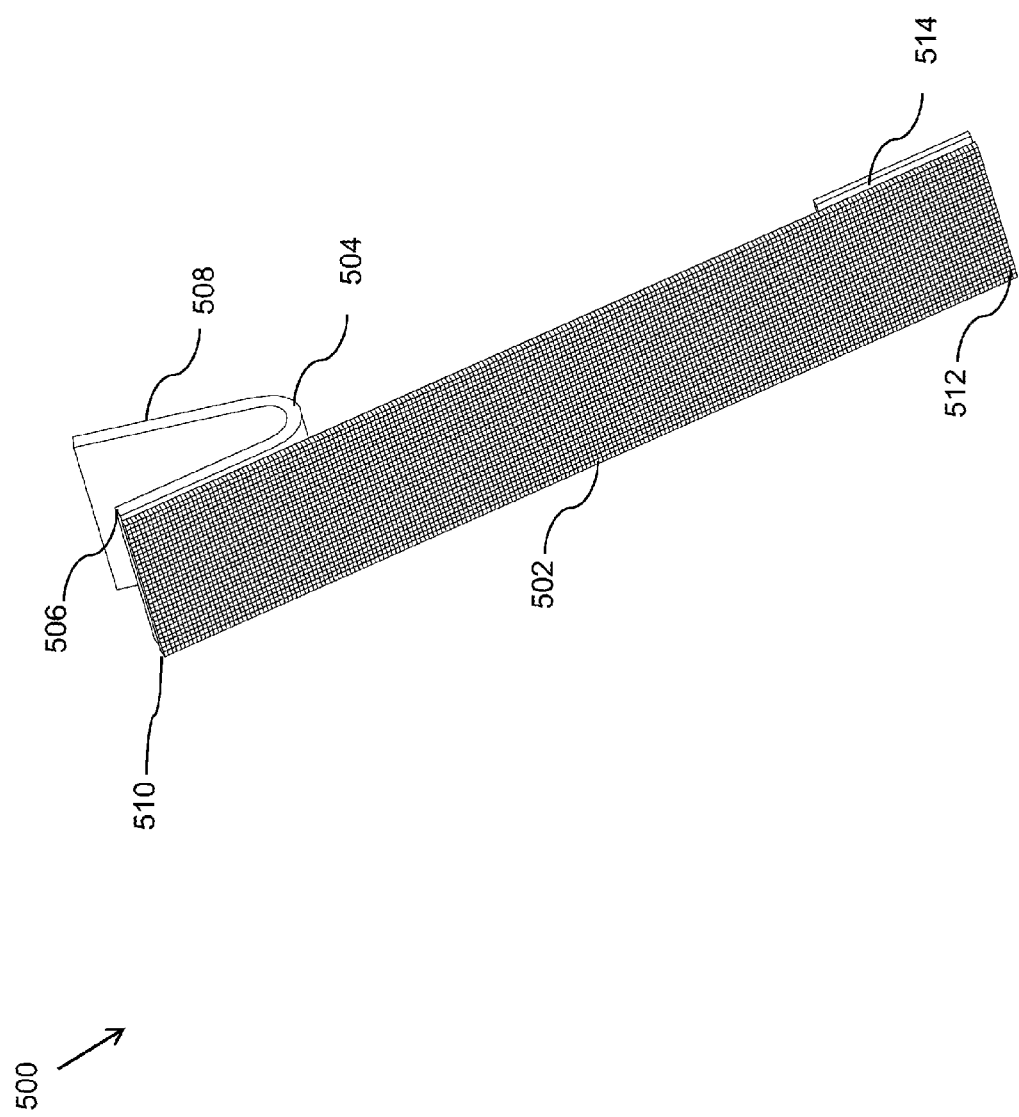

FIGS. 5A and 5B are perspective views of a medical device 500 in accordance with an embodiment of the present invention. The medical device 500 includes a first elongate member 502, a second elongate member 504, and a third elongate member 514. The second elongate member 504 includes a first portion 506 and a second portion 508. The first elongate member 502 and the second elongate member 504 are similar to the first elongate members and the second elongate members described in conjunction with FIGS. 1, 2, and 3.

In accordance with various embodiments, since the second portion 508 is attached with the first portion 506 at only one of its transverse edges, it is free to move or rotate with respect to the first portion 506 and can take a defined shape based on an anatomical location. The defined shape formed by moving/rotating the second portion 508 with respect to the first portion 506 is non-planar and can be modified based on the anatomical location of the patient where the first portion 506 and the second portion 508 are attached. In some embodiments, the defined shape can be a U shape as illustrated in FIGS. 5A and 5B. These figures illustrate a perspective view of the medical device 500 with the second elongate member 504 forming a U shape. FIG. 5A illustrates the perspective view taken at an angle and FIG. 5B illustrates the perspective view taken at another angle.

In some embodiments, the second portion 508 of the second elongate member 504, which is attached to the first portion 506 of the second elongate member 504, is malleable. The malleable second portion 508 would allow the surgeon/operator to mould the second portion 508 over a portion of the vaginal vault as per the requirement of the patient's anatomy.

The third elongate member 514 is made of a biologic material. A few examples of biological materials have been discussed above. In accordance with some embodiments, the third elongate member 514 is a strip with its length substantially more than its width. In certain embodiments, the third elongate member 514 is rectangular in shape. In other embodiments, the third elongate member 514 may have other shapes. In accordance with some embodiments, the width of the third elongate member 514 is uniform from its proximal end portion 510 to its distal end portion 512. In other embodiments, the width of the third elongate member 514 varies from the proximal end portion 510 to the distal end portion 512. The third elongate member is discussed in conjunction with FIG. 1 also.

In some embodiments, the third elongate member 514 is attached to the first elongate member 502 separately by an operator. In other embodiments, the third elongate member 514 can form a part of the medical device 500 as such without separately attaching the third elongate member 514. The third elongate member 514 can be attached to the distal end portion 512 of the first elongate member 502 in a planar manner such that the third elongate member 514 is not movable with respect to the first elongate member 502, through various attachment elements along the length. In some embodiments, the attachment elements include without limitations sutures, adhesives, bonding agents, mechanical fasteners (e.g. a medical grade plastic clip), and the like.

The third elongate member 514 is configured to be attached to a third bodily portion. In some embodiments, the third bodily portion is a sacrum.

Figure 6A:
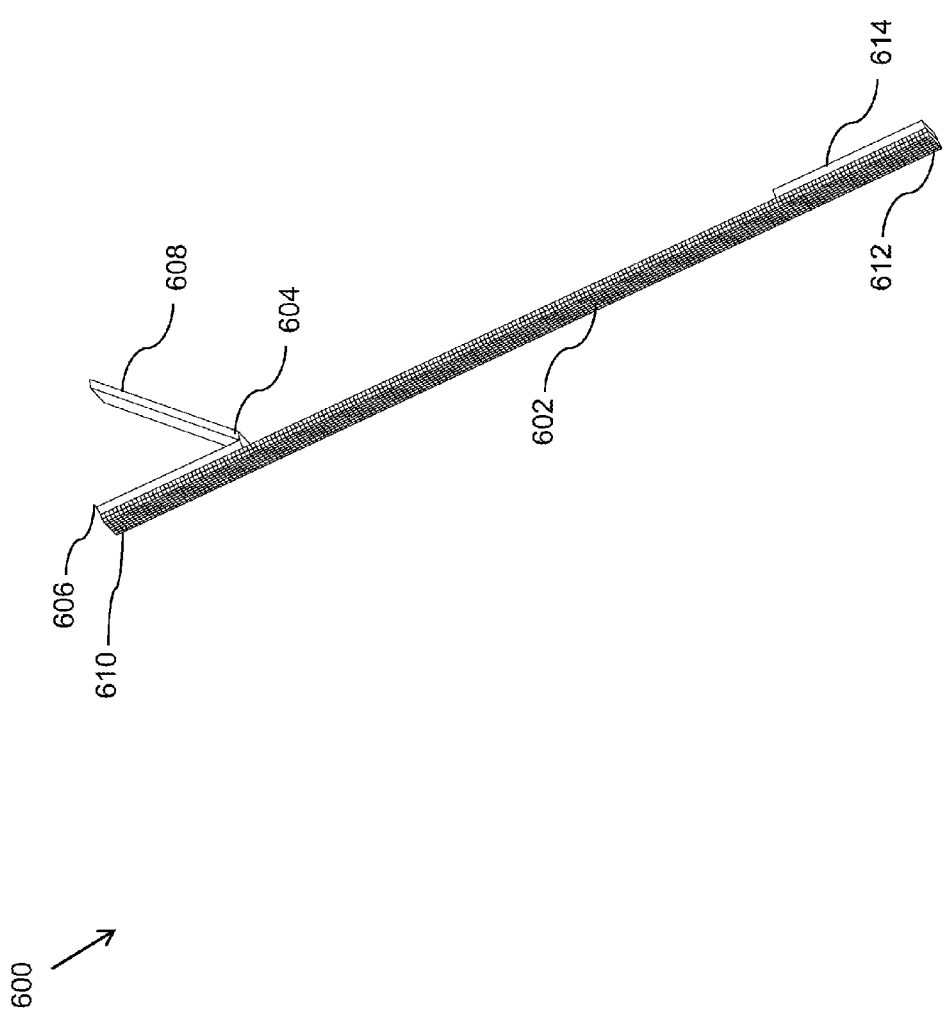
FIGS. 6A and 6B are perspective views of a medical device in accordance with an embodiment of the present invention.
Figure 6B:
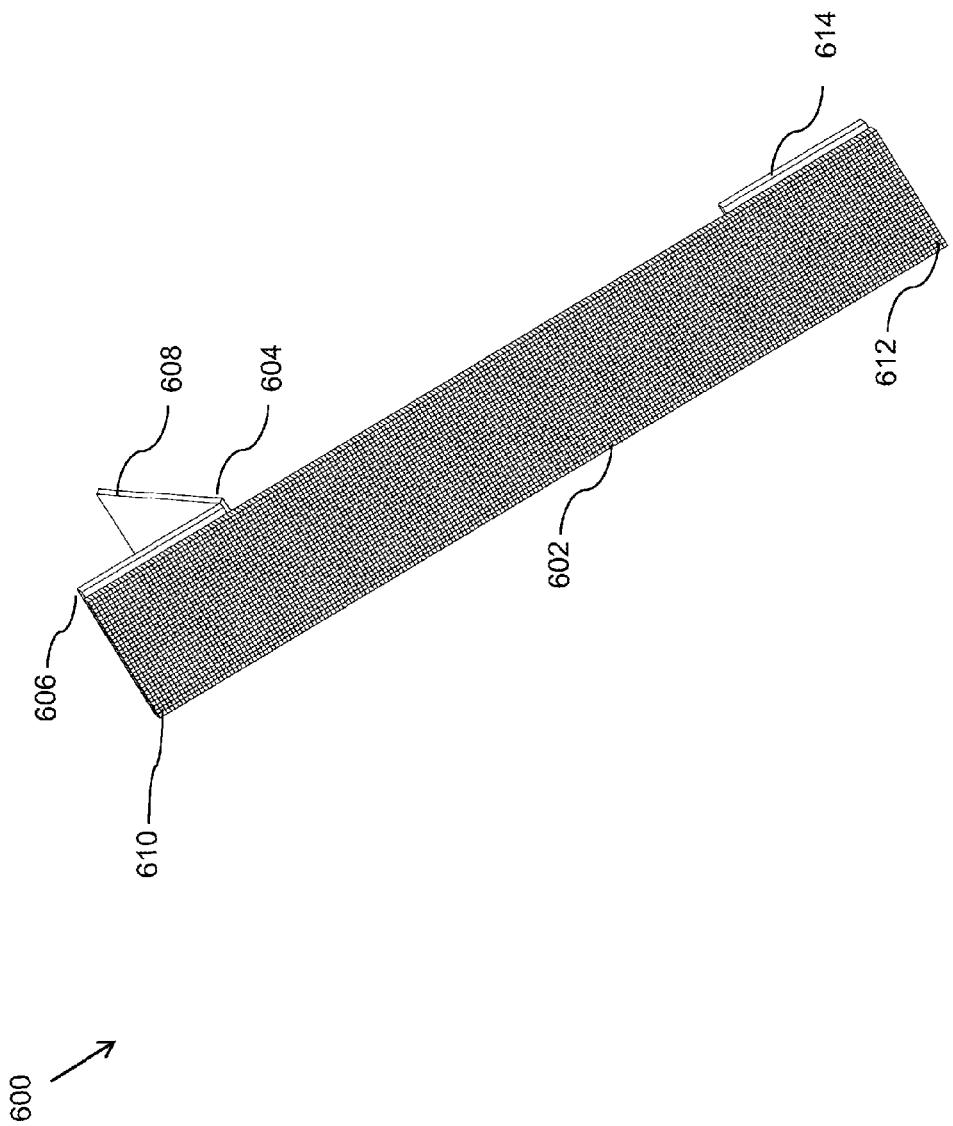

FIGS. 6A and 6B are perspective views of a medical device 600 in accordance with an embodiment of the present invention. The medical device 600 includes a first elongate member 602 having a proximal end portion 610 and a distal end portion 612, a second elongate member 604, and a third elongate member 614. The second elongate member 604 includes a first portion 606 and a second portion 608. The first elongate member 602, the second elongate member 604, and the third elongate member 614 are similar to the first elongate members, the second elongate members, and the third elongate members described in conjunction with FIGS. 1, 4A, and 4B.

In accordance with various embodiments, since the second portion 508 is attached with the first portion 506 at only one of its transverse edges, it is free to move or rotate with respect to the first portion 506 and can take a defined shape based on an anatomical location. The defined shape formed by moving/rotating the second portion 508 with respect to the first portion 506 is non-planar and can be modified based on the anatomical location of the patient where the first portion 506 and the second portion 508 are attached. In some embodiments, the defined shape can be a V shape as illustrated in FIGS. 6A and 6B. These figures illustrate perspective views of the medical device 600 with the second elongate member 604 forming a V shape. FIG. 6A illustrates the perspective view taken at an angle and FIG. 6B illustrates the perspective view taken at another angle.

In some embodiments, the second portion 608 of the second elongate member 604, which is attached to the first portion 606 of the second elongate member 604, is malleable. The malleable second portion 608 would allow the surgeon/operator to shape the second portion 608 over a portion of the vaginal vault as per the requirement of the patient's anatomy.

FIG. 7 is a perspective view of a medical device 700 in accordance with an embodiment of the present invention. The medical device 700 includes a first elongate member 702 and a second elongate member 704.

As illustrated in FIG. 7, the first elongate member 702 includes a proximal end portion 706 and a distal end portion 708. The various shapes and dimensions of the first elongate member 702 have been discussed above in conjunction with FIGS. 1 and 2. In accordance with the illustrated embodiment, the first elongate member 702 and second elongate member 704 are made of soft, pliable acellular tissues that are biologic materials. As shown, the second elongate member 704 is directly attached to the first elongate member 702 at its proximal end 706 through one of its transverse edges.

In accordance with various embodiments, since the second elongate member 704 is attached with the first elongate member 702 at only one of its transverse edges, it is free to move or rotate with respect to the first elongate member 702 and can take a defined non-planar shape. The defined shape formed by moving/rotating the second elongate member 704 with respect to the first elongate member 702 and can be modified based on the anatomical location of the patient where the first elongate member 702 and the second elongate member 704 are attached. In some embodiments, the defined shape can be a V shape as illustrated in FIG. 7.

In some embodiments, the second elongate member 704, which is attached to the first elongate member 702, is malleable in nature. The malleable second elongate member 704 would allow the surgeon/operator to shape the second elongate member 704 over a portion of the vaginal vault as per the requirement of the patient's anatomy. As the first elongate member 702 and the second elongate member 704 are made of biologic materials, the surgeon/operator may need to hydrate them before the surgical procedure.

Figure 8:
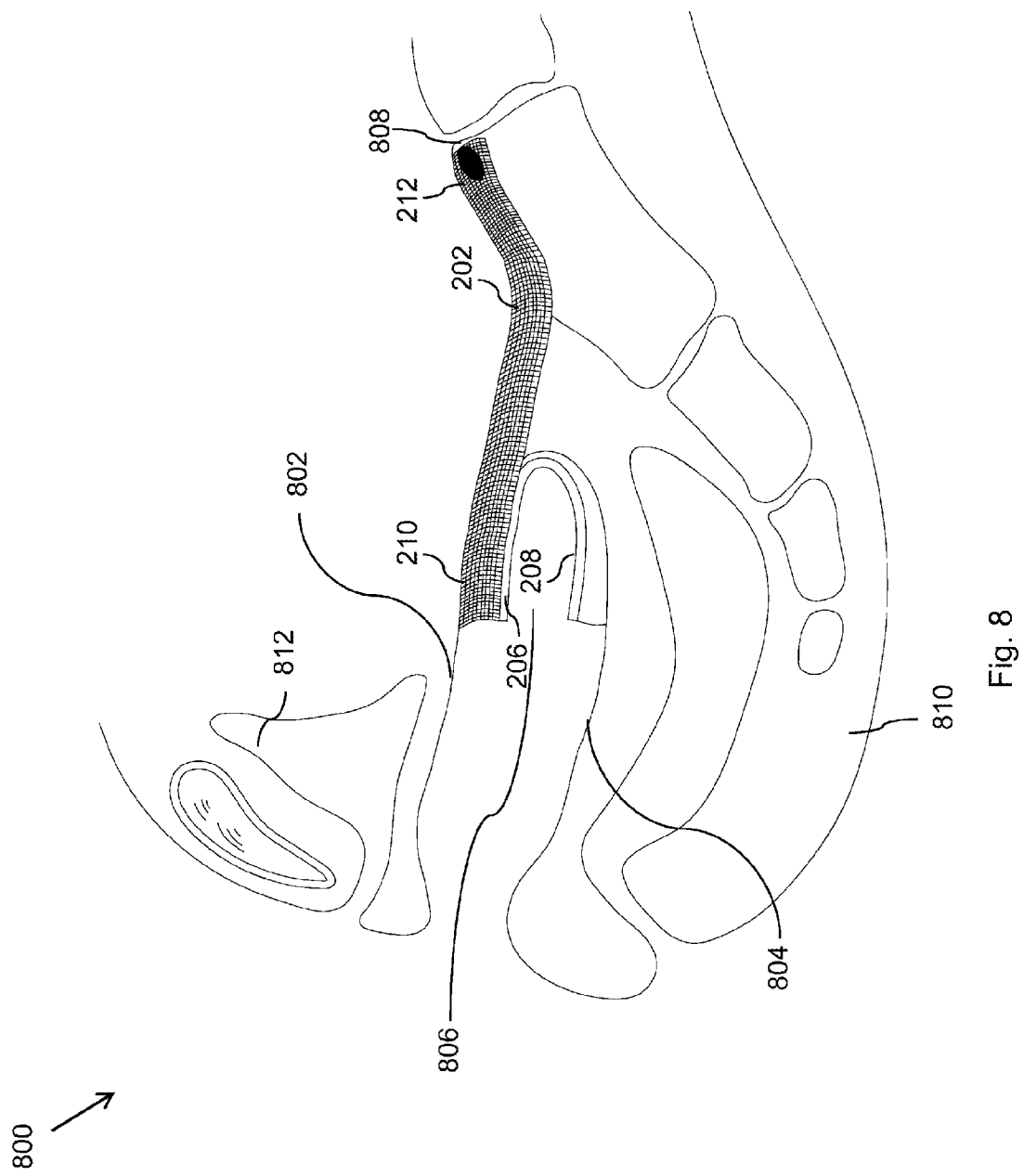
FIG. 8 illustrates placement of the medical device, in accordance with an embodiment of the present invention.

FIG. 8 illustrates placement of the medical device 200 within a patient's body, in accordance with an embodiment of the present invention. The medical device 200 is used hereafter to describe the placement within the body. However, it must be appreciated that other medical devices such as the medical device 100, medical device 400, medical device 500, medical device 600, and the medical device 700 may also be employed. The body portions of the patient such as an anterior vaginal wall 802, a posterior vaginal wall 804, a vagina 806, a sacrum 808, buttocks 810, and a bladder 812 are also illustrated in FIG. 8.

As shown, the first portion 206 of the second elongate member 204 is attached to the exterior surface of an anterior vaginal wall 802 and the second portion 208 of the second elongate member 204 is attached to the exterior surface of a posterior vaginal wall 804. The distal end portion 212 of the first elongate member 202 is attached to the sacrum 808 of the patient. In some other embodiments, it can be attached to any other location close to the sacrum 808. The second elongate member 204 of the medical device 200 can be flipped around such that it extends to the exterior surface of the posterior vaginal wall 804 along the anatomy of the patient's vaginal walls. In some embodiments, the first elongate member 202 is made of a synthetic material such as polypropylene and the second elongate member 204 is made of a biologic material such as bovine dermis, porcine dermis, and the like as discussed in conjunction with FIG. 3. In other embodiments, the first elongate member 702 and the second elongate member 704 are made of biologic materials as discussed in FIG. 7.

As shown, the first portion 206 and the second portion 208 of the second elongate member 204 form a U shape in accordance with the illustrated embodiment. In accordance with other embodiments, the first portion 206 and the second portion 208 of the second elongate member 204 can form a V shape. The V shape is discussed above in conjunction with FIG. 4.

Figure 9:
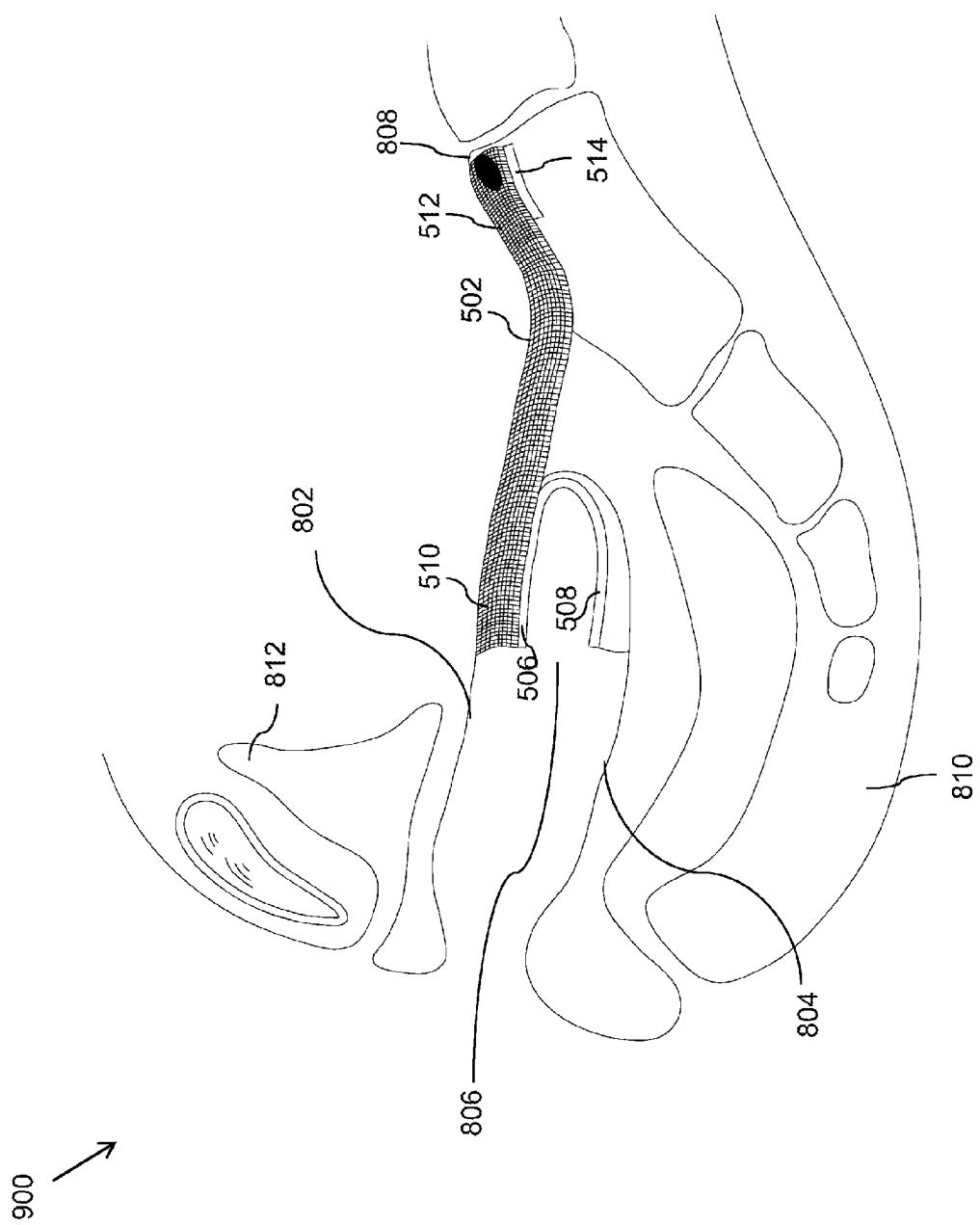
FIG. 9 illustrates placement of the medical device, in accordance with an embodiment of the present invention.

FIG. 9 illustrates a perspective view of the placement of the medical device 500 within a patient's body, in accordance with another embodiment of the present invention.

The first portion 506 of the second elongate member 504 is attached to the exterior surface of an anterior vaginal wall 802 and the second portion 508 of the second elongate member 504 is attached to the exterior surface of a posterior vaginal wall 804. In other embodiments, the second elongate member 204 of the medical device 200 is attached to the exterior surface of the posterior vaginal wall 804 and the first portion 506 of the second elongate member 504 is attached to the exterior surface of the posterior vaginal wall. The third elongate member 514, which is attached to the first elongate member 502 at its distal end portion 512, is configured to be attached to the sacrum 808 of the patient. In some other embodiments, it can be attached to any other location close to the sacrum 808 (such as to bodily tissue proximate the sacrum 808). In some embodiments, the third elongate member 514 is attached to the first elongate member 502 separately by an operator. In other embodiments, the third elongate member can form a part of the medical device 100 such that the operator can use the medical device 100 as such as such without separately attaching the third elongate member 514.

In some embodiments, the first portion 506 and the second portion 508 of the second elongate member 504 and the third elongate member 514 are designed in shape and length in accordance with the anatomical structure of the coupling locations/bodily tissues at the anterior vaginal wall 802, posterior vaginal wall 804, and the sacrum 808, respectively. In some embodiments, the first elongate member 502 is made of a synthetic material such as polypropylene, and the second elongate member 504 and the third elongate member 514 are made of a biologic material such as bovine dermis, porcine dermis, and the like as discussed in conjunction with FIG. 5. In other embodiments, the first elongate member 702 and the second elongate member 704 are made of biologic material as discussed in conjunction with FIG. 7. The first portion 506 and the second portion 508 of the second elongate member 504 form a U shape in accordance with the illustrated embodiment. In accordance with other embodiments, the first portion 506 and the second portion 508 of the second elongate member 504 can form a V shape. The U and V shapes of the medical device have been described in conjunction with FIGS. 3A-7.

FIG. 10 is a flowchart illustrating a method 1000 of placement of a medical device such as the medical device 200, in accordance with an embodiment of the present invention.

Referring to FIG. 10 in conjunction with FIGS. 8 and 9, the method of placement of the medical device 200 is described in accordance with an embodiment of the present invention. The medical device 200 is hereafter used to describe the placement in an exemplary embodiment. However, it must be appreciated that other medical devices such as the medical devices 100, 400, 500, 600, and 700 may also be placed in the similar manner.

The method 1000 includes creating an abdominal/vaginal access to the vagina 806 of a patient for delivery of the medical device 200 at step 1002. The medical device 200 includes the first elongate member 202 and the second elongate member 204. The first elongate member 202 includes the proximal end portion 210 and the distal end portion 212. The second elongate member 204 includes the first portion 206 and the second portion 208. The medical device 200 has been described in conjunction with FIGS. 2-3B. In accordance with various embodiments, an operator/surgeon may make incisions laproscopically, laprotomically, or in any other manner to create access to the vagina 806. Once the access to the vagina 806 is created, the medical device 200 is inserted into the patient's body at step 1004.

Subsequently, the first portion 206 of the second elongate member 204 is attached to the first bodily portion at step 1006. In some embodiments, the first bodily portion is the anterior vaginal wall 802. In some embodiments, the first elongate member 202 is designed in shape and length in accordance with the anatomical structure of the coupling locations (where the elongate member is coupled/attached to the bodily tissues) at the anterior vaginal wall 802.

The second portion 208 of the second elongate member 204 is then attached to the second bodily portion at step 1008. In some embodiments, the second bodily portion is the posterior vaginal wall 804. In some embodiments, the second elongate member 204 is designed in shape and length in accordance with the anatomical structure of the coupling locations (where the elongate member is coupled/attached to the bodily tissues) at the posterior vaginal wall 804. The second elongate member 204 is made of a biologic material as discussed above. In other embodiments, the first elongate member 202 and the second elongate member 204 can be made of biologic materials.

In some embodiments, the medical device may also include the third elongate member such as the third elongate member 514 or the third elongate member 614 as shown in FIGS. 5A, 5B, 6A, and 6B. In accordance with these embodiments, the method of placement of the medical device may further include attaching the third elongate member 514 to the sacrum 808 of the patient.

In accordance with various embodiments, upon placement, the first portion such as the first portion 506 of the second elongate member 504, the second portion such as the second portion 508 of the second elongate member 504, and the third elongate member such as the third elongate member 514 act as different arms of the defined non-planar shape that are configured to support the pelvic organs at distinct bodily locations. In accordance with these embodiments, the first portion 506 forms a first arm of the defined shape, the second portion 508 forms a second arm of the defined shape and the third elongate member 514 forms a third arm of the defined shape.

In accordance with some embodiments, the method of placement of the medical device may further include hydration of the biological material of the elongate members 202 and 204 before delivery inside the patient's body. Typically, the elongate members made of biologic materials are kept dry before use in order to maintain sterility. Sufficient hydration of the biologic material is required to produce lubrication and tissue turgor during implantation. Hydration of the biologic material enhances the malleability of the elongate members; therefore, the elongate members that are made of biologic material can be shaped according to the specific anatomical locations where they are attached upon hydration. In some embodiments, the elongate members made of biologic materials can be dipped in a saline solution for hydration.

In some embodiments, a medical device is configured to be delivered and placed within a patient's body. The medical device includes a first elongate member and a second elongate member. The first elongate member has a proximal end portion and a distal end portion. The first elongate member is made of a first material. The second elongate member is made of a second material different than the first material. The second elongate member has a first portion and a second portion such that the first portion of the second elongate member is attached to the first elongate member and the second portion of the second elongate member is attached to the first portion of the second elongate member at one of its transverse edges. The first portion and the second portion of the second elongate member are configured to form a defined non-planar shape. The first portion being a first arm of the defined non-planar shape and the second portion being a second arm of the defined non-planar shape.

In some embodiments, the first portion of the second elongate member is configured to be attached to a first bodily portion. In some embodiments, the first bodily portion is an anterior vaginal wall. In some embodiments, the second portion of the second elongate member is configured to be attached to a second bodily portion. In some embodiments, the second bodily portion is a posterior vaginal wall. In some embodiments, the first material is synthetic. In some embodiments, the synthetic material includes polypropylene. In some embodiments, the first portion of the second elongate member and the second portion of the second elongate member forms an integral part of the second elongate member. In some embodiments, the first portion of the second elongate member is removably coupled to the second portion of the second elongate member.

In some embodiments, the defined non-planar shape is a U shape. In some embodiments, the defined non-planar shape is a V shape. In some embodiments, the second material includes a biologic material. In some embodiments, the biologic material comprises a bovine dermis, a porcine dermis, a cellulose based product, an allograft, a cadaveric tissue.

In some embodiments, the device includes a third elongate member coupled to the distal end portion of the first elongate member. In some embodiments, the third elongate member forms a part of the medical device such that the medical device is configured to be directly placed within the patient's body. In some embodiments, the third elongate member is coupled to the first elongate member separately by an operator.

In some embodiments, the third elongate member is made of a biologic material. In some embodiments, the biologic material comprises a bovine dermis, a porcine dermis, a cellulose based product, an allograft, a cadaveric tissue. In some embodiments, the third elongate member is configured to be attached to a third bodily portion. In some embodiments, the third bodily portion is a sacrum of the patient.

In some embodiments, the medical device is a bodily implant configured to support bodily tissues for the treatment of pelvic floor prolapse.

In some embodiments, a medical device configured to be delivered and placed within a patient's body includes a first elongate member, a second elongate member, and a third elongate member. The first elongate member has a proximal end portion and a distal end portion. The first elongate member is made of a synthetic material. The second elongate member is made of a biologic material. The second elongate member has a first portion and a second portion such that the first portion of the second elongate member is attached to the first elongate member and the second portion of the second elongate member is attached to the first portion of the second elongate member at one of its transverse edges. The second portion of the second elongate member is movable with respect to the first portion of the second elongate member such that the second elongate member is configured to form a defined non-planar shape. The third elongate member is made of a biologic material. The third elongate member is attached to the distal end portion of the first elongate member in a planar manner such that the third elongate member is not movable with respect to the first elongate member.

In some embodiments, the second portion of the second elongate member is configured to be attached to a posterior vaginal wall. In some embodiments, the first portion of the second elongate member is configured to be attached to an anterior vaginal wall. In some embodiments, the third elongate member is configured to be attached to a sacrum of the patient.

In some embodiments, a method of implanting a medical device in a patient's body, the method includes creating an access to a vagina of the patient for delivery of the medical device, the medical device having a first elongate member made of a first material and a second elongate member made of a second material different than the first material, the second elongate member having a first portion and a second portion such that the first portion of the second elongate member is attached to the first elongate member and the second portion of the second elongate member is attached to the first portion of the second elongate member at one of its transverse edge, the first portion and the second portion of the second elongate member being configured to form a defined shape, the first portion being a first arm of the defined shape and the second portion being a second arm of the defined shape; inserting the medical device into the patient's body; attaching the first portion of the second elongate member to a first bodily portion; and attaching the second portion of the second elongate member to a second bodily portion.

In some embodiments, the first bodily portion is an anterior vaginal wall. In some embodiments, the second bodily portion is a posterior vaginal wall.

In some embodiments, the device includes a third elongate member, the method further comprising attaching the third elongate member to a third bodily portion.

In some embodiments, the third bodily portion is a sacrum.

In some embodiments, the first material is synthetic. In some embodiments, the second material is a biologic material.

In some embodiments, the method includes hydrating the medical device before delivery inside the patient's body.

In some embodiments, the access is created abdominally. In some embodiments, the access is created vaginally.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device configured to be delivered and placed within a patient's body, the medical device comprising:
   a first elongate member having a proximal end portion and a distal end portion, the first elongate member being made of a first material; and
   a second elongate member made of a second material different than the first material, the second elongate member having a length smaller than the first elongate member, the second elongate member having a first portion and a second portion, the second portion of the second elongate member directly extending from a transverse edge of the first portion, the transverse edge being perpendicular to a central axis extending along a length of the second elongate member,
   wherein only the first portion of the second elongate member is directly attached to a surface of the first elongate member at the proximal end portion of the first elongate member, the second portion of the second elongate member being deflectable away from the surface of the first elongate member, the first portion and the second portion of the second elongate member being configured to form a defined non-planar shape, the first portion being a first arm of the defined non-planar shape and the second portion being a second arm of the defined non-planar shape.

2. The medical device of claim 1, wherein the first portion of the second elongate member is configured to be attached to a first bodily portion.

3. The medical device of claim 2, wherein the first bodily portion is an anterior vaginal wall.

4. The medical device of claim 1, wherein the second portion of the second elongate member is configured to be attached to a second bodily portion.

5. The medical device of claim 4, wherein the second bodily portion is a posterior vaginal wall.

6. The medical device of claim 1, wherein the first material is synthetic.

7. The medical device of claim 1, wherein the first portion of the second elongate member is parallel to the first elongate member.

8. The medical device of claim 1, wherein the first portion of the second elongate member and the second portion of the second elongate member forms an integral part of the second elongate member.

9. The medical device of claim 1, wherein the first portion of the second elongate member is removably coupled to the second portion of the second elongate member.

10. The medical device of claim 1, wherein the defined non-planar shape is a U shape.

11. The medical device of claim 1, wherein the defined non-planar shape is a V shape.

12. The medical device of claim 1, wherein the first material includes a polymeric mesh, and the second material includes a biologic material.

13. The medical device of claim 12, wherein the biologic material comprises one of a bovine dermis, a porcine dermis, a cellulose based product, an allograft, a cadaveric tissue.

14. The medical device of claim 1 further comprising a third elongate member coupled to the distal end portion of the first elongate member, the third elongate member being coupled to a surface of the distal end portion of the first elongate member.

15. The medical device of claim 14, wherein the third elongate member forms a part of the medical device such that the medical device is configured to be directly placed within the patient's body.

16. The medical device of claim 14, wherein the third elongate member is coupled to the first elongate member separately by an operator.

17. A medical device configured to be delivered and placed within a patient's body, the medical device comprising:
   a first elongate member having a proximal end portion and a distal end portion, the first elongate member being made of a synthetic material;
   a second elongate member made of a biologic material, the second elongate member having a length smaller than the first elongate member, the second elongate member having a first portion and a second portion, the first portion of the second elongate member being attached to the first elongate member, the second portion of the second elongate member directly extending from a transverse edge of the first portion, the transverse edge being perpendicular to a central axis extending along a length of the second elongate member, only the first portion of the second elongate member being directly attached to a surface of the first elongate member at the proximal end portion of the first elongate member, the second portion of the second elongate member being deflectable away from the surface of the first elongate member, the second elongate member configured to form a defined non-planar shape by movement of the second portion of the second elongate member with respect to the first portion of the second elongate member, and a third elongate member made of a biologic material, wherein the third elongate member is fixedly attached to the distal end portion of the first elongate member in a planar manner.

18. The medical device of claim 17, wherein the second portion of the second elongate member is configured to be attached to a posterior vaginal wall.

19. The medical device of claim 17, wherein the first portion of the second elongate member is configured to be attached to an anterior vaginal wall.

20. A method of implanting a medical device in a patient's body, the method comprising:

creating an access to a vagina of the patient for delivery of the medical device, the medical device having a first elongate member made of a first material and a second elongate member made of a second material different than the first material, the second elongate member having a length smaller than the first elongate member, the second elongate member having a first portion and a second portion, the first portion of the second elongate member being attached to the first elongate member, the second portion of the second elongate member directly extending from a transverse edge of the first portion, the transverse edge being perpendicular to a central axis extending along a length of the second elongate member, only the first portion of the second elongate member being directly attached to a surface of the first elongate member at the proximal end portion of the first elongate member, the second portion of the second elongate member being deflectable away from the surface of the first elongate member, the first portion and the second portion of the second elongate member being configured to form a defined shape, the first portion being a first arm of the defined shape and the second portion being a second arm of the defined shape;

inserting the medical device into the patient's body;

attaching the first portion of the second elongate member to a first bodily portion; and attaching the second portion of the second elongate member to a second bodily portion.

* * * * *